United States Patent
Pageat (10) Patent No.: US 9,675,066 B2
(45) Date of Patent: Jun. 13, 2017

(54) FELINE SCRATCH MARKING SEMIOCHEMICALS

(71) Applicant: Institut de Recherche en Semiochimie et Ethologie Appliquee, Saint Sarturnin d'Apt (FR)

(72) Inventor: Patrick Pageat, Route de Saint-Saturnin APT (FR)

(73) Assignee: Institut de Recherche en Semiochimie et Ethologie Appliquee, Saint Saturnin d'Apt (FR)

( * ) Notice: Subject to any disclaimer, the term of this patent is extended or adjusted under 35 U.S.C. 154(b) by 0 days.

(21) Appl. No.: 15/069,825

(22) Filed: Mar. 14, 2016

(65) Prior Publication Data

US 2016/0192650 A1    Jul. 7, 2016

Related U.S. Application Data

(62) Division of application No. 13/532,388, filed on Jun. 25, 2012, now Pat. No. 9,314,018.

(51) Int. Cl.
| | |
|---|---|
| *A61K 35/12* | (2015.01) |
| *A61K 35/26* | (2015.01) |
| *A61K 35/36* | (2015.01) |
| *A01N 37/02* | (2006.01) |
| *A01N 37/36* | (2006.01) |
| *A01N 63/02* | (2006.01) |
| *A01K 15/02* | (2006.01) |
| *A01N 37/06* | (2006.01) |
| *A01N 65/22* | (2009.01) |

(52) U.S. Cl.
CPC .......... *A01N 37/02* (2013.01); *A01K 15/024* (2013.01); *A01N 37/06* (2013.01); *A01N 37/36* (2013.01); *A01N 63/02* (2013.01); *A01N 65/22* (2013.01)

(58) Field of Classification Search
CPC ......... A61K 35/26; A61K 35/36; A61K 36/12
USPC ................................ 424/537, 574
See application file for complete search history.

(56) References Cited

U.S. PATENT DOCUMENTS

| | | | |
|---|---|---|---|
| 2,005,817 | A | 6/1935 | Yoder |
| 3,963,833 | A | 6/1976 | DeSalva et al. |
| 3,993,027 | A | 11/1976 | Mullin |
| 4,852,518 | A * | 8/1989 | Yananton ............ A01K 1/0107 119/169 |
| 5,258,176 | A | 11/1993 | Keenan |
| 5,567,436 | A | 10/1996 | Udelle |
| 5,709,863 | A | 1/1998 | Pageat |
| 6,054,481 | A | 4/2000 | Pageat |
| 6,077,867 | A | 6/2000 | Pageat |
| 6,169,113 | B1 | 1/2001 | Pageat |
| 6,345,593 | B1 | 2/2002 | Stewart et al. |
| 6,384,252 | B1 | 5/2002 | Pageat |
| 7,723,388 | B2 | 5/2010 | Pageat |
| 2003/0166688 | A1 | 9/2003 | Soll et al. |
| 2005/0137119 | A1 | 6/2005 | Pageat |
| 2006/0046988 | A1 | 3/2006 | Boeckh et al. |
| 2008/0292560 | A1 | 11/2008 | Tamarkin et al. |
| 2008/0299220 | A1 | 12/2008 | Tamarkin et al. |
| 2010/0210584 | A1 | 8/2010 | Borge et al. |
| 2011/0077301 | A1 * | 3/2011 | Deminiere ............ A61K 9/007 514/549 |
| 2011/0162587 | A1 | 7/2011 | Hass et al. |
| 2013/0023490 | A1 | 1/2013 | Boeckh et al. |
| 2013/0323194 | A1 | 12/2013 | Everhart |

OTHER PUBLICATIONS

Munger et al., "An Electron Microscopic Study of Eccrine Sweat Glands of the Cat Foot and Toe Pads—Evidence for Ductal Reabsorption in the Human," The Journal of Biophysical and Biochemical Cytology, 1961; 11: 403-417.

Rustan et al., "Fatty Acids: Structure and Properties," Encyclopedia of Life Science, 2005; 1-7.

Foster, K.G., J. Physiol. 1966. vol. 184, pp. 106-119.

* cited by examiner

*Primary Examiner* — Chris R Tate
(74) *Attorney, Agent, or Firm* — Venable LLP; Keith G. Haddaway; Miguel A. Lopez (57) ABSTRACT

Semiochemical compositions comprising a feline scratch marking semiochemical analogs of these semiochemical compositions and a method to prevent cats from scratching in particular places and on multiple objects are described.

10 Claims, 5 Drawing Sheets

FELINE SCRATCH MARKING SEMIOCHEMICALS

CROSS-REFERENCE TO RELATED APPLICATION

This application is a divisional of U.S. application Ser. No. 13/532,388, filed Jun. 25, 2012, the entire disclosure of the foregoing application being incorporated herein by reference.

FIELD OF THE INVENTION

The present invention relates to semiochemical compositions comprising a feline scratch marking semiochemical analogues of these semiochemical compositions and a method to prevent cats from scratching in particular places and on multiple objects.

BACKGROUND AND PRIOR ART

Cats are known for their scratching behavior, which is seen by most cat owners as one of the most unacceptable nuisance in this species. Most cat owners misunderstand this behavior interpreting it as a sole means for controlling the length of their claws. However, cats usually scratch for three reasons: to hone or sharpen their claws, which are the cat's chief offensive and defensive weapons, to stretch and tone their muscles and to mark their territory.

Felines actually have sweat glands in their paw pads and when they scratch against furniture, curtains, wallpaper, corners of upholstered furniture and other objects they are actually depositing their own scent onto those objects. Vertical scratches also leave a visible mark for other cats to see as well as to smell. Thus, there are actually two different marks that cats make when they scratch various objects; a visible marking and an odorous marking.

Currently to rid felines of scratching various objects it is suggested that the feline be trained to scratch in particular areas by providing scratching posts, scratching pads or cat trees. Other alternatives are herbal sprays that repel the felines from objects due to their scent or double-sided tape. Herbal sprays replace the odorous territorial markers left behind by the scratching to discourage repeat scratching in the same place. Since cats' paws are extremely sensitive to touch, using sticky surfaces, such as double-sided tape, is exceptionally annoying to cats so that they avoid touching those surfaces.

Soft plastic nail caps called Softpaws® are also available which should be applied to the claws every 4 to 6 weeks and keep the nails blunt. However, the application of these plastic nail caps is difficult, since they are applied with glue. Usually they are applied by an expert or veterinarian.

Electric carpets are yet another solution. These carpets are placed by the objects that are being scratched and discharge a strong electric volts but weak amperage in the footpads of the cats that walk on them.

Yet another alternative is to dull the cat's claws by trimming their nails as a part of a general routine or declawing the cat. However these solutions are not really recommended by veterinarian's since it may lead to other behavioral problems in cats.

U.S. Pat. No. 5,709,863 discloses compositions containing an emulsion and a mixture of fatty acids or derivatives thereof and a compound of vegetal origin that has an attractive effect on cats for preventing cats from urinating in a marked spot or to prevent anxiety in cats. These compositions comprise an emulsion of oleic acid, azelaic acid, palmitic acid, pimelic acid and a compound of vegetal origin that has an attractive effect on cats. However, this patent does not solve the problem of preventing cats from scratching on multiple objects.

Thus, there is a need in the art to address the problem of feline's scratching on multiple household and other objects.

It is object of the present invention to provide an alternative treatment for preventing cats to scratch on multiple objects.

It is another object to provide compositions that attract cats to a particular object which the cat can scratch.

It is another object to provide a scratching post that attracts cats and thus prevents them from scratching other multiple objects.

It is yet another object to provide a method of attracting cats to a particular object so that they can scratch that object, while avoiding other objects.

These and other objects are achieved by the present invention as evidenced by the summary of the invention, description of the preferred embodiments and the claims.

SUMMARY OF THE PRESENT INVENTION

In one of the composition aspects, the present invention provides a semiochemical composition comprising a secretion obtained from the interdigital paws of a cat.

In another aspect a semiochemical composition comprising valeric acid, lactic acid and linoleic acid and/or derivatives thereof and/or isomers thereof is provided.

A semiochemical composition comprising between about 3.5% to 10.5% (w %/w %) of valeric acid, between about 5.5% to 15.5% (w %/w %) of lactic acid and between 68.5% to 83.5 (w %/w %) of linoleic acid and/or derivatives thereof and/or isomers thereof is yet another aspect of the invention.

In another aspect a semiochemical composition comprising between about 3.5% to 10.5% (w %/w %) of valeric acid, between about 5.5% to 15.5% (w %/w %) of lactic acid, between about 48.4% to 58.9% (w %/w %) of linoleic acid and between about 20.1% to 24.5% (w %/w %) of oleic acid and/or derivatives thereof and/or isomers thereof is provided.

The present invention provides a semiochemical composition analogue comprising 10% to 20% (w %/w %) of valeric acid, lactic acid and linoleic acid and/or derivatives thereof and/or isomers thereof and 60% to 98% (w %/w %) of linoleic acid.

A semiochemical composition analogue comprising 10% to 20% (w %/w %) of a composition comprising between about 3.5% to 10.5% (w %/w %) of valeric acid, between about 5.5% to 15.5% (w %/w %) of lactic acid and between 68.5% to 83.5 (w %/w %) of linoleic acid and/or derivatives thereof and/or isomers thereof and between 60% to 98% (w %/w %) of linoleic acid is yet another embodiment of the present invention.

In another embodiment a semiochemical composition comprising 20% of a composition comprising between about 3.5% to 10.5% (w %/w %) of valeric acid, between about 5.5% to 15.5% (w %/w %) of lactic acid and between 68.5% to 83.5 (w %/w %) of linoleic acid and/or derivatives thereof and/or isomers thereof and 75% linoleic acid.

Solutions of the above described semiochemical compositions and analogues thereof are also one aspect of the present invention.

The semiochemical compositions can further comprise a solvent and optionally at least one cat attractant and colorants.

A method for preventing a cat from scratching on multiple objects, said method comprising placing at least one semiochemical composition and/or semiochemical composition analogues and/or derivatives thereof and/or isomers thereof on an object that a cat uses for scratching.

A cat scratching post, board, carpet, trees and toys comprising the semiochemical compositions or semiochemical composition analogues, and/or derivatives thereof and/or isomers thereof as described herein, are also an aspect of the present invention.

DETAILED DESCRIPTION OF THE PREFERRED EMBODIMENTS

As used herein "semiochemical" means a chemical emitted by a plant or an animal that evokes a behavioral or physiological response in another organism. When the semiochemical affects an individual of the same species, it is called a pheromone. When the semiochemical affects an individual of a different species, it is called an allelochemical.

By "enhancer composition" is meant an active semiochemical composition or analogues thereof that is species-specific in cats and which can be used to enhance or act synergistically with the basic semiochemical composition or analogues thereof and/or derivatives thereof and/or isomers thereof to increase the effectiveness in felines of the basic semiochemical composition or analogues thereof.

The terms cats and felines are used interchangeably herein. "Feline" means of or belonging to the family Felidae, which includes lions, tigers, jaguars and wild and domestic cats.

The term "object or objects" means any physical thing that can be seen and touched. Examples of objects includes any object that a feline may scratch including, but limited to, rugs, furniture, carpets, drapes, upholstered corners of couches and chairs, wall papered surfaces, cardboard storage boxes, wood trim on doors and walls. These are only a very few examples defined to encompass the term objects that is used herein.

As used herein the term "analogue" means a group of chemical compounds similar in structure but different in respect to an elemental composition.

"Derivatives of fatty acids" as used herein includes fatty acid esters, salts, alcohols, ketones, ethers and amides.

By "isomers" is meant herein a chemical species with the same number and types of atoms as another chemical species and include conjugated fatty acids, which are positional and geometric isomers. Due to the configuration of the double bond in some fatty acids, they can take two forms. The cis form, in which both of the hydrogen atoms are on the same side of the chain and the trans form in which the hydrogen atoms are on opposite sides. For example, conjugated linoleic acid is a mixture of positional and geometric isomers of linoleic acid involving double bonds at positions 8 and 10, 9 and 11, 10 and 12 or 11 and 13. Each of these positional diene isomers can occur in cis-trans, trans-cis, cis-cis or trans-trans geometrical configurations.

The term "consisting essentially of" means that the semiochemical compositions or analogues thereof and/or derivatives thereof and/or isomers thereof can contain other ingredients that do not affect the semiochemical properties of the compositions or analogues thereof.

More specifically, the present invention relates to semiochemical compositions derived from the interdigital area of the cat's paws that is used to attract the cat's to a specific area for scratching.

Analogues, derivatives and isomers of the semiochemical compositions, described herein, are also encompassed by the present invention.

The compositions and analogues of the present invention are based on semiochemical compositions and made up of volatile molecules, the essential components of these molecules being fatty acids and methyl esters of the fatty acids.

In one aspect, the composition of the present invention comprises a mixture of three fatty acids; namely valeric acid, lactic acid and linoleic acid and/or derivatives thereof and/or isomers thereof which represent between about 3.5% to 83.5% (w %/w %) of the total composition. The remaining ingredients being compounds having an attractive affect on cats, colorants and solvents.

In another aspect the semiochemical composition comprises a mixture of propionic acid, cyclohexylacetic acid and cyclopentylproprionic acid and/or derivatives thereof and/or isomers thereof, which represents between 11.5% to 45.5% (w %/w %) of the total composition. This composition can also contain compounds that have an attractive affect on cats, colorants and solvents.

In yet another aspect the semiochemical composition comprises a mixture of valeric acid, lactic acid, linoleic acid and oleic acid and/or derivatives thereof and/or isomers thereof, which represents between 5.5% to 58.9% (w %/w %) of the total composition.

The semiochemical analogues of the present invention comprise 10% to 20% (w %/w %) of a mixture of three fatty acids; namely valeric acid, lactic acid and linoleic acid and/or derivatives thereof and/or isomers thereof and from 60% to 98% (w %/w %) of linoleic acid.

The semiochemical analogues or semiochemical compositions or derivatives thereof and/or isomers thereof can be attached to a chemical carrier provided that the bioactive structure of the fatty acids is preserved. Such carrier molecules include resins, liposomes, crown compounds, proteins, polymers and the like.

The fatty acids can be in their pure form, i.e., as a free fatty acid as well as their derivatives forms such as esters of fatty acids, salts of fatty acids, alcohols of fatty acids, ketones of fatty acids, ethers of fatty acids, and amides of fatty acids.

Isomers of the fatty acids in the semiochemical compositions and/or derivatives and/or analogues thereof, described herein, can also be used in the formulations of the semiochemical compositions.

More specifically, the semiochemical compositions of the present invention comprise between about 3.5% to 10.5% (w %/w %) valeric acid, between about 5.5% to 15.5% (w %/w %) lactic acid and between 68.5% to 83.5% (w %/w %) linoleic acid and/or derivatives thereof and/or isomers thereof.

A solution of a semiochemical compositions comprising between about 3.5% to 10.5% (w %/w %) valeric acid, between about 5.5% to 15.5% (w %/w %) lactic acid and between 68.5% to 83.5% (w %/w %) linoleic acid and/or derivatives thereof and/or isomers thereof is also encompassed by the present invention.

In one aspect the semiochemical compositions of the present invention comprise between about 3.5% to 10.5% (w %/w %) valeric acid, between about 5.5% to 15.5% (w %/w %) lactic acid and between 68.5% to 83.5% (w %/w %) linoleic acid and/or isomers thereof and/or derivatives thereof that are esters, salts, alcohols, ketones, ethers and amides of valeric acid, lactic acid and linoleic acid. These derivatives are in the same percentages as their fatty acid compositions.

A solution of the semiochemical compositions of the present invention comprise between about 3.5% to 10.5% (w %/w %) valeric acid, between about 5.5% to 15.5% (w %/w %) lactic acid and between 68.5% to 83.5% (w %/w %) linoleic acid and/or isomers thereof and/or derivatives thereof that are esters, salts, alcohols, ketones, ethers and amides of valeric acid, lactic acid and linoleic acid. These derivatives are in the same percentages as their fatty acid compositions.

Another embodiment of the present invention is a semiochemical composition comprising between about 3.5% to 10.5% (w %/w %) of valeric acid, between about 5.5% to 15.5% (w %/w %) of lactic acid, between about 48.4% to 58.9% (w %/w %) of linoleic acid and between about 20.1% to 24.5% (w %/w %) of oleic acid and/or derivatives thereof and/or isomers thereof.

A solution of the semiochemical composition comprising between about 3.5% to 10.5% (w %/w %) of valeric acid, between about 5.5% to 15.5% (w %/w %) of lactic acid, between about 48.4% to 58.9% (w %/w %) of linoleic acid and between about 20.1% to 24.5% (w %/w %) of oleic acid and/or derivatives thereof and/or isomers thereof is part of the present invention.

Another embodiment of the present invention is a semiochemical composition comprising between about 3.5% to 10.5% (w %/w %) of valeric acid, between about 5.5% to 15.5% (w %/w %) of lactic acid, between about 48.4% to 58.9% (w %/w %) of linoleic acid and between about 20.1% to 24.5% (w %/w %) of oleic acid and/or isomers thereof and derivatives thereof that are esters, salts, alcohols, ketones, ethers and amides of valeric acid, lactic acid, linoleic acid and oleic acid. These derivatives are in the same percentage as their fatty acid counterparts.

In yet another aspect of the present invention a solution of the semiochemical composition comprising between about 3.5% to 10.5% (w %/w %) of valeric acid, between about 5.5% to 15.5% (w %/w %) of lactic acid, between about 48.4% to 58.9% (w %/w %) of linoleic acid and between about 20.1% to 24.5% (w %/w %) of oleic acid and/or isomers thereof and/or derivatives thereof that are esters, salts, alcohols, ketones, ethers and amides of valeric acid, lactic acid, linoleic acid and oleic acid. These derivatives are in the same percentage as their fatty acid counterparts.

In another aspect the semiochemical compositions of the present invention comprises a composition comprising about 36.5% to 43.5% (w %/w %) propionic acid, about 11.5% to 26.5% (w %/w %)cyclohexylacetic acid and about 33.5% to 45.5% (w %/w %) cyclopentylproprionic acid and/or derivatives thereof and/or isomers thereof. These derivatives are in the same percentage as their fatty acid counterparts.

A solution of the semiochemical composition comprising about 36.5% to 43.5% (w %/w %) propionic acid, about 11.5% to 26.5% (w %/w %) cyclohexylacetic acid and about 33.5% to 45.5% (w %/w %) cyclopentylproprionic acid and/or derivatives thereof and/or isomers thereof is another aspect of the invention. These derivatives are in the same percentage as their fatty acid counterparts.

In yet another aspect the semiochemical compositions of the present invention comprise about 36.5% to 43.5% (w %/w %) propionic acid, about 11.5% to 26.5% (w %/w %) cyclohexylacetic acid and about 33.5% to 45.5% (w %/w %) cyclopentylproprionic acid and/or isomers thereof and/or derivatives thereof that are esters, salts, alcohols, ketones, ethers and amides of propionic acid, cyclohexylacetic acid and cyclopentylpropionic acid. These derivatives are in the same percentage as their fatty acid counterparts.

A solution of semiochemical compositions of the present invention comprise about 36.5% to 43.5% (w %/w %) propionic acid, about 11.5% to 26.5% (w %/w %) cyclohexylacetic acid and about 33.5% to 45.5% (w %/w %) cyclopentylproprionic acid and/or isomers thereof and/or derivatives thereof that are esters, salts, alcohols, ketones, ethers and amides of propionic acid, cyclohexylacetic acid and cyclopentylpropionic acid is yet another aspect of the invention. These derivatives are in the same percentage as their fatty acid counterparts.

The present invention provides a semiochemical composition analogue comprising 10% to 20% (w %/w %) of valeric acid, lactic acid and linoleic acid and/or derivatives thereof and/or isomers thereof and 60% to 98% (w %/w %) of linoleic acid.

In yet another aspect analogues of the semiochemical composition comprises between about 3.5% to 10.5% (w %/w %) valeric acid, between about 5.5% to 15.5% (w %/w %) lactic acid and between 68.5% to 83.5% (w %/w %) linoleic acid and/or derivatives thereof and/or isomers thereof in concentrations of 10% to 20% (w %/w %) and between 60% to 98% (w %/w %) of linoleic acid. These derivatives are in the same percentage as their fatty acid counterparts.

A solution of the semiochemical composition comprising between about 3.5% to 10.5% (w %/w %) valeric acid, between about 5.5% to 15.5% (w %/w %) lactic acid and between 68.5% to 83.5% (w %/w %) linoleic acid and/or derivatives thereof and/or isomers thereof in concentrations of 10% to 20% (w %/w %) and between 60% to 98% (w %/w %) of linoleic acid is part of the present invention. These derivatives are in the same percentage as their fatty acid counterparts.

In yet another aspect analogues of the semiochemical composition comprises between about 3.5% to 10.5% (w %/w %) valeric acid, between about 5.5% to 15.5% (w %/w %) lactic acid (w %/w %) and between 68.5% to 83.5% (w %/w %) of linoleic acid in concentrations of 10% to 20% and between 60% to 98% (w %/w %) of linoleic acid and/or isomers thereof and/or derivatives thereof that are esters, salts, alcohols, ketones, ethers and amides of valeric acid, lactic acid and linoleic acid. These derivatives are in the same percentage as their fatty acid counterparts.

In another aspect a solution of the semiochemical composition comprises between about 3.5% to 10.5% (w %/w %) valeric acid, between about 5.5% to 15.5% (w %/w %) lactic acid and between 68.5% to 83.5% (w %/w %) linoleic acid in concentrations of 10% to 20% (w %/w %) and between 60% to 98% (w %/w %) of linoleic acid and/or isomers thereof and/or derivatives thereof that are esters, salts, alcohols, ketones, ethers and amides of valeric acid, lactic acid and linoleic acid forms part of the invention.

In one embodiment the semiochemical analogues such as SC10-98, which has 10% of the fraction Sc1 (See, Table III below) and 98% linoleic acid; SC10-75, which has 10%, of the fraction Sc1 (See, Table III below) and 75% linoleic acid; SC10-60, which has 10% of the fraction Sc1 (See, Table III below) and 60% linoleic acid; SC20-98, which has 20% of the fraction Sc1 (See, Table III below) and 98% linoleic acid; SC20-75, which has 20% of the fraction Sc1 (See, Table III below) and 75% linoleic acid; and SC20-60, which has 20% of the fraction Sc1 (See, Table III below) and 60% linoleic acid form another aspect of the semiochemical compositions of the invention.

Solutions of the semiochemical analogues such as SC10-98, which has 10% of the fraction Sc1 (See, Table III below) and 98% linoleic acid; SC10-75, which has 10%, of the fraction Sc1 (See, Table III below) and 75% linoleic acid; SC10-60, which has 10% of the fraction Sc1 (See, Table III below) and 60% linoleic acid; SC20-98, which has 20% of the fraction Sc1 (See, Table III below) and 98% linoleic acid; SC20-75, which has 20% of the fraction Sc1 (See, Table III below) and 75% linoleic acid; and SC20-60, which has 20% of the fraction Sc1 (See, Table III below) and 60% linoleic acid form another aspect of the invention.

The semiochemical compositions described herein can be diluted in various solvents and can be used in various forms. The compositions may be in the form of a solution, aerosol spray, gel, slow release matrix, microencapsulated product, liposomes, nanoparticles and the like.

In a preferred embodiment the fatty acids can be microencapsulated and put into a suspension in alcohol.

An enhancer composition containing between 5% to 35% (w %/w %) can also be added to the semiochemical composition, if desired. This enhancer composition comprises volatile organic compounds and mixtures thereof and includes, but not limited to amines and fatty acids from indolic derivatives, esters of these amines and fatty acids, ketones such as acetone, alcohols, sterols and the like.

Cat attractants can also be optionally added to the composition. These include catnip (*Nepeta Cataria*), essential oil of catnip, tatarian honeysuckle (*Lonicera tartarica*), Valerian (*Valerriana officicinalis*), silver vine/matatabi (*Actinidia polygama*), cat thyme (*Teucrium marum*), Buckbean (*Menyanthes trifoliate*), actinidine, actinidiolide, boschnialactone, boschniakine, dihydroactinidiolide, dihydronepetalactone, epinepetalactone, iridomyrmecin, isodihydronepetalactone, missugashiwalactone, neonepetalactone, onikulactone and mixtures thereof.

The cat attractants are present in the semiochemical compositions described herein in an amount of 0.05% to 0.15% (w %/w %). The cat attractants can also be present in the amount of 0.02% to 0.20% (w %/w %). They also can be present in the amount of 0.01% to 0.10% (w %/w %).

The concentration of the above-mentioned fatty acids may vary depending on the final form of use. However, the concentrations of the specific fatty acids that may be utilized and their concentration may be ascertained and tested according to the methods set forth herein.

The fatty acids, which are generally solid in nature, can be diluted in any nonaqueous solvent to form a solution of the present invention. More particularly, solvents such as ethyl alcohol, propylene glycol, alcohol, ether, chloroform, ethanol, benzene, acetone, propyl alcohol, isopropanol, 2-propanol fixed and volatile oils and the like. It is preferable to use ethyl alcohol in the formulation or acetone and propylene glycol. The ethyl alcohol can be 95% ethyl alcohol.

Fatty acids are commercially available from various chemical companies in solid form. However, since it is difficult to solubilize fatty acids, the fatty acid is generally added to the solvent under constant agitation and at a temperature of between about 37° C. to about 38° C., more preferably 37.5° C.

The semiochemical compositions and analogues, as well as their derivatives and isomers, described herein, can be applied to scratching posts or cat trees or any object in which the cat has a tendency to scratch. For example, cat platforms, cat carpets, cat boards, cat toys and the like. Thus, the cat is attracted by the semiochemical compositions, analogues, derivatives and isomers and using that semiochemical coated object to scratch and tends not to scratch other objects that the cat had a habit to do prior to the semiochemical usage.

The above-described compositions were discovered after the detailed analysis of the interdigital area of cat's paws. This procedure involved recuperating from surfaces where the cats scratched secretions and analyzing the chemical composition of these secretions via mass spectroscopy or gas chromatography/mass spectroscopy.

A first secretion called fraction Sc1 and a second secretion called Sc2 were obtained after analysis. Several analogues based on the Sc1 fraction and linoleic acid were also tested for their effectiveness to prevent cat's from scratching multiple objects. These analogues contained various amounts of the Sc1 fraction and differing amounts of linoleic acid.

The present invention also relates to a method of preventing cats from scratching on multiple objects, said method comprising placing one of the semiochemical compositions, analogues, derivatives and/or isomers of the present invention, as described herein, on an object such that the cat is attracted to the object and scratches on this objection and not other objects.

Cat posts, cat platforms, cat carpets, cat boards, cat toys and the like, having the semiochemical compositions, analogues, derivatives and isomers, as described herein, placed on these objects also forms a part of the invention.

In order to illustrate the present invention and the advantages thereof, the following specific examples are given, it being understood that the same are intended only as illustrative and in nowise limitative.

EXAMPLE 1

A Population Study

The cats that were chosen for this study based on the major genetic branching and ethnic classification of cats. The three major types of cats that were chosen for this study were European cats, Siamese cats and Persian cats. The sex of the cats that were chosen for this study included females (F), castrated females (CF), males (M) and castrated males (CM).

The cats constituted twelve groups with five cats per group. This population was considered as an initial survey. The results obtained showed a large heterogeneity in the secretion compositions based either on the individual cats or their race. Therefore the sampling had to be repeated with a larger cat population.

Besides the criteria of race and sex, other criteria were established to be included in the dozen groups which were: (1) registered in a studbook kept by one of the recognized breeding clubs; (2) have an age between 8 months and 5 years; (3) did not receive any medical treatment for the last 3 months; (4) did not have any commercial cat scratching post; (5) did not use any litter that was chemical or perfumed; the cat litter had to be constituted of pure clay; (6) did not present any symptom of anxiety; (7) the scratch marking had to be executed every day on the same posts in proximity of a territorial zone in which the cat badly tolerated intrusions that is verified by a territorial aggression during an intrusion; and (8) the cat had a behavior of scratching that was observed at least one time per day by its owners and for at least one month.

The following Table I shows the cats that were selected for this study.

TABLE I

| NUMBER & TYPE OF CATS | SEX | AGE IN MONTHS | DURATION OF SCRATCHING IN MONTHS |
|---|---|---|---|
| EUR1 | M | 12 | 3 |
| EUR2 | FC | 9.5 | 4 |
| EUR3 | FC | 11 | 2 |
| EUR4 | MC | 25 | 5 |
| EUR5 | MC | 9 | 3.5 |
| EUR6 | M | 12.5 | 2 |
| EUR7 | F | 11 | 1.5 |
| EUR8 | FC | 10 | 2 |
| EUR9 | MC | 9.5 | 3.5 |
| EUR10 | F | 11.5 | 3 |
| EUR11 | M | 10.5 | 3 |
| EUR12 | M | 11 | 2.5 |
| EUR13 | F | 12 | 4 |
| EUR14 | MC | 15 | 2 |
| EUR15 | FC | 18 | 1.5 |
| EUR16 | F | 11.5 | 6 |
| EUR17 | MC | 9.5 | 2 |
| EUR18 | F | 18.5 | 3 |
| EUR19 | M | 21 | 5 |
| EUR20 | FC | 14 | 3 |
| SIA1 | FC | 9.5 | 9 |
| SIA2 | MC | 11 | 4 |
| SIA3 | MC | 13.5 | 4 |
| SIA4 | FC | 12 | 2.5 |
| SIA5 | F | 14 | 2 |
| SIA6 | M | 17 | 5 |
| SIA7 | F | 9 | 3 |
| SIA8 | F | 10.5 | 2 |
| SIA9 | M | 12 | 2 |
| SIA10 | MC | 18 | 2 |
| SIA11 | FC | 14.5 | 7 |
| SIA12 | FC | 9 | 6.5 |
| SIA13 | M | 11 | 3 |
| SIA14 | MC | 16.5 | 2 |
| SIA15 | FC | 12 | 4 |
| SIA16 | F | 10.5 | 6 |
| SIA17 | M | 13 | 2.5 |
| SIA18 | F | 18.5 | 3 |
| SIA19 | MC | 20 | 2 |
| SIA20 | M | 14 | 8 |
| PER1 | MC | 9.5 | 6 |
| PER2 | F | 10 | 4 |
| PER3 | M | 11 | 3.5 |
| PER4 | MC | 10.5 | 2 |
| PER5 | FC | 14 | 3 |
| PER6 | FC | 16 | 2.5 |
| PER7 | F | 18 | 4 |

TABLE I-continued

| NUMBER & TYPE OF CATS | SEX | AGE IN MONTHS | DURATION OF SCRATCHING IN MONTHS |
|---|---|---|---|
| PER8 | M | 22 | 3 |
| PER9 | F | 17 | 7 |
| PER10 | M | 9.5 | 2.5 |
| PER11 | F | 10 | 2 |
| PER12 | MC | 12.5 | 5 |
| PER13 | MC | 16 | 6 |
| PER14 | M | 15.5 | 4 |
| PER15 | M | 18 | 3 |
| PER16 | MC | 9 | 2 |
| PER17 | FC | 20 | 8 |
| PER18 | FC | 21.5 | 4 |
| PER19 | F | 12.5 | 1.5 |
| PER20 | FC | 11 | 3 |

The homogeneity of the groups were confirmed by the student T test which gave the following results for age and race and for duration of scratching and race.

Unpaired T-Test for AGE with the Variable Group of RACE with a Theoretical Gap of 0

| cat origin | average difference | Degrees of Freedom DDL | t | p |
|---|---|---|---|---|
| European, Siamese | −0.176 | 38 | −0.145 | 0.8855 |
| European, Persian | −1.075 | 38 | −0.795 | 0.4313 |
| Siamese, Persian | −0.899 | 38 | −0.753 | 0.4562 |

Information of the Group by AGE Variable Group of RACE

| cats origin | number | average | variance | standard deviation | standard error |
|---|---|---|---|---|---|
| European | 20 | 13.100 | 18.674 | 4.321 | 0.966 |
| Siamese | 20 | 13.276 | 10.693 | 3.270 | 0.731 |
| Persian | 20 | 14.175 | 17.849 | 4.225 | 0.945 |

Unpaired t-Test for DURATION OF SCRATCHING with a Variable Group of RACE with a Theoretical Gap of 0

| origin of cats | average difference | Degrees of Freedom DDL | t | p |
|---|---|---|---|---|
| European, Siamese | −0.900 | 38 | −1.589 | 0.1203 |
| European, Persian | −0.725 | 38 | −1.495 | 0.1431 |
| Siamese, Persian | 0.175 | 38 | 0.276 | 0.7842 |

Information of the DURATION OF SCRATCHING Group with a Variable Group of RACE

| origin of cats | number | average | variance | standard deviation | standard error |
|---|---|---|---|---|---|
| European | 20 | 3.075 | 1.534 | 1.238 | 0.277 |
| Siamese | 20 | 3.975 | 4.881 | 2.209 | 0.494 |
| Persian | 20 | 3.800 | 3.168 | 1.780 | 0.398 |

EXAMPLE 2

Isolation and Analysis to Identify the Semiochemical Associated with Cat's Scratching Isolation To assure that the secretions were taken which were spontaneously deposited by the cats a device was used that permitted to obtain the scratches on a support that was compatible with the requirements of chemical analysis.

The samples were taken during a period of 48 hours by fixing a surgical compress using latex examining gloves on part of the surface lacerated by the cat.

The lacerated surface was divided in two in the sense of the height. One of the two halves was recovered with the aid of a sterile compress. To ensure that there was not any dissymmetry in the deposit of the secretion, the sample was collected alternatively half left and half right at each site for two days to collect the pheromones.

The sterile compresses that were collected were replaced every 6 hours during the day at the same hour that the owners went to sleep and woke up. This represented 9 compresses per day per cat, thus 18 compresses on average per cat during two days of collection. During the collection, the sterile compresses were manipulated with gloved hands and immediately placed in a flask that contained 10 ml of acetonitrile. This solvent was the one that was utilized during the analysis of the samples.

The flasks distributed to the cat's owners carried a coded number associated with their animal at the moment of recruitment. Each owner returned 5 flasks that contained 3 to 4 sterile compresses.

During this collection phase, if the compresses came torn off from their support in the course of the execution of scratching and were found on the ground during collecting, they were eliminated from the study to not risk the contamination of the samples with other material. In the course of this study 9 sterile compresses had to be eliminated.

Analysis

The solvent used throughout this study was HPLC grade acetonitrile (CH3CN) that is commercialized by SIGMA (catalogue number 43,913-4). The samples were treated by differentiating the groups to which the individual cats belonged. For each cat, the samples which were taken over a 48 hour period were mixed.

The sterile compresses were first mixed with the aid of a glass stirrer that was washed and rinsed with acetonitrile prior to inserting the samples from another cat. 30 ml of solution was obtained for each cat. 10 ml of each solution was evaporated under a nitrogen stream prior to being diluted in 1 ml of acetonitrile to realize a 10-fold concentration.

The samples were then subjected to gas chromatography/mass spectroscopy using a Turbo Mass spectrometer made by Perkin Elmer. The detection was effectuated on impact using (EI+) at an energy of 70 eV at 180° C. A JW column type DB1 having a length of 60 m (id=0.25 mm film=0.25 μm) at a split of ½₀ and a split/splitless of 3 seconds was used. 1.0 μl from the sample was injected.

The initial results were analyzed using a data base to obtain the most probable spectrums. Data bases containing such data are well known in the art.

The initial results obtained with the 60 chromatographic profiles presented little differences between the cats. These chromatographs contained 11 chemical substances, which were uniquely typical fatty acids or fatty acids in the form of methyl esters. Four of the seven fatty acids were in the form of an ester, which leads to the number of 11 components. These 11 components are set forth in Table II below

TABLE II

| Compounds | Formula |
| --- | --- |
| proprionic acid | $C_2H_5CO_2H$ |
| lactic acid | $CH_3CH(OH)CO_2H$ |
| valeric acid | $CH3(CH_2)_3CO_2H$ |
| methyl valerate | $CH_3(CH_2)_3CO_2CH_3$ |
| isovaleric acid | $(CH_3)_2CHCH_2CO_2H$ |
| cyclohexylacetic acid | $C_6H_{11}CH_2CO_2H$ |
| methyl cyclohexylacetate | $C_6H_{11}CH_2CO_2CH_3$ |
| 3-cyclopentylproprionic acid | $C_5H_9CH_2CH_2CO_2H$ |
| methyl 3-cyclopentylpropionate | $C_5H_9CH_2CH_2CO_2CH_3$ |
| linoleic acid | $CH_3(CH_2)_4CH=CHCH_2CH=CH(CH_2)_7CO_2H$ |
| methyl linoleate | $CH_3(CH_2)_4CH=CHCH_2CH=CH(CH_2)_7CO_2CH3$ |

Since isovaleric acid was only present in 34% of cats it was excluded in the specific secretions. Also excluded were the esters since they could be considered as degradation products of the semiochemical secretion due to cutaneous bacteria. The secretions can also undergo a biotransformation due to symbiotes or saprophytes before acquiring their active structure. In this the transformation of the pro-semiochemical is important and goes in the direction of simplifying the structure. This is what happens in the anal sacks of carnivores. The glands excrete proteins that are transformed into amines by the local saprophytes. In this case, the passage of the fatty acid to its methyl ester does not affect very much the spatial structure of the fatty acid, which is merely anecdotal and therefore permits to increase the portion of the fatty acids due to the ester.

Two fractions were identified having six different fatty acids. One fraction Sc1 was present in 69% to 83% of the total secretions. This fraction was called Sc1 and its compounds are present in Table III. The second faction Sc2 was very rare and never appeared alone in the population of cats that was studied. Sc2 was present in the total secretions between 17% and 31%. Sc2 was present in cats that were more stressed during the study. The compounds of Sc2 are presented in Table IV.

TABLE III

| Compounds | Amounts in wt %/wt % |
| --- | --- |
| valeric acid | 3.5 to 10.5% |
| lactic acid | 5.5 to 15.5% |
| linoleic acid | 68.5 to 83.5% |

TABLE IV

| Compounds | Amounts in wt %/wt % |
|---|---|
| propionic acid | 36.5% to 43.5% |
| cyclohexylacetic acid | 11.5% to 26.5% |
| cyclopentylproprionic acid | 33.5% to 45.5% |

EXAMPLE 3

Testing of the Structural Analogues of the Cat Scratching Semiochemical 70 cats were tested in this study using the solution SC10-98, SC10-75, SC10-60, SC20-98, SC20-75 and SC20-60, which are structural analogues of the feline scratch marking pheromone. SC10-98 had 10% of the fraction Sc1 (See, Table III above) and 98% linoleic acid; SC10-75 had 10% of the fraction Sc1 (See, Table III above) and 75% linoleic acid; SC10-60 had 10% of the fraction Sc1 (See, Table III above) and 60% linoleic acid; SC20-98 had 20% of the fraction Sc1 (See, Table III above) and 98% linoleic acid; SC20-75 had 20% of the fraction Sc1 (See, Table III above) and 75% linoleic acid; and SC20-60 had 20% of the fraction Sc1 (See, Table III above) and 60% linoleic acid.

Ethanol was used as a placebo, which was the same solvent used in the solutions. This study was not conducted as a double blind study since although the six analogues could not be distinguished by the human nose, the ethanol could in fact be distinguished. However the treatment was conducted randomly.

For this study the analogues of the feline scratch marking semiochemical were applied to a new cat scratching post for cats that were habituated to scratch another object.

The cats for this study were pets from the Paris area. To be included in the study, besides their approval from their owners, the cats must have satisfied the following conditions: (1) cats of all different races; (2) castrated or non-castrated males and females; (3) the minimum age was 9 months and the maximum age was 8 years; (4) have no signs of an ailment and have not been treated; and (5) the cat scratched at a specific site constantly for a period of at least 2 months.

The criteria for non-inclusion were (1) that the cats had onychetomies (declawed); (2) the cats were in any bad health; (3) the cats were undergoing an intervention during the 7 days of the test; (4) the cats were carriers of torn nail sheaths; and (5) the cats underwent behavioral therapy for scratching.

The criteria for exclusion included (1) occurrence of any organic disease; (2) the cats underwent anesthesia; (3) the cats were administered drugs with the exception of intern and extern antiparasites; (4) any modification of the cats environment including moving; and (5) introducing a new animal into the household.

70 cats were used in this study; 10 cats for each treatment. E stands for European S stands for Siamese and P stands for Persian. The treatment and background of each cat that was tested is set forth in Table V below.

TABLE V

| CATS | RACE | SEX | AGE in months | DURATION OF SCRATCHING IN MONTHS | TREATMENT GIVEN |
|---|---|---|---|---|---|
| C1 | E | M | 9 | 2 | SC10-60 |
| C2 | S | MC | 12 | 3 | SC20-98 |
| C3 | E | MC | 11 | 4 | SC20-60 |
| C4 | E | FC | 28 | 11 | SC10-75 |
| C5 | E | FC | 26 | 15 | P |
| C6 | S | MC | 33 | 24 | SC20-75 |
| C7 | S, E | F | 21 | 15 | SC20-98 |
| C8 | SB | FC | 14 | 6 | P |
| C9 | E | MC | 9.5 | 2 | SC20-60 |
| C10 | S | MC | 12.5 | 3 | SC10-98 |
| C11 | P | FC | 11.5 | 2 | SC10-75 |
| C12 | E | MC | 14.5 | 5 | SC20-75 |
| C13 | P | M | 17 | 3 | SC20-75 |
| C14 | P, E | FC | 14 | 2 | SC10-60 |
| C15 | E | FC | 15.5 | 3 | SC20-60 |
| C16 | P | F | 16 | 6 | SC20-98 |
| C17 | P, E | MC | 10 | 2 | P |
| C18 | E | MC | 10.5 | 4 | SC10-60 |
| C19 | S | MC | 15 | 5 | P |
| C20 | P, E | M | 16.5 | 6 | SC10-98 |
| C21 | SB | FC | 14.5 | 8 | SC10-75 |
| C22 | SB, E | FC | 46 | 38 | SC20-98 |
| C23 | P | FC | 36.5 | 28 | SC10-60 |
| C24 | P | F | 25 | 11 | SC10-98 |
| C25 | E | MC | 33 | 25 | SC20-60 |
| C26 | P | MC | 32.5 | 24 | SC20-75 |
| C27 | P, E | MC | 18 | 11 | SC10-98 |
| C28 | E | FC | 16.5 | 8 | SC20-98 |
| C29 | E | FC | 62 | 54 | SC20-75 |
| C30 | E | F | 65.5 | 58 | SC10-75 |
| C31 | E | FC | 23.5 | 16 | SC10-60 |
| C32 | S, E | MC | 36.5 | 29 | SC10-75 |
| C33 | SB | MC | 42.5 | 37 | P |
| C34 | P | M | 41 | 34 | SC10-98 |
| C35 | E | MC | 25 | 16 | SC20-75 |
| C36 | P, E | MC | 33.5 | 25 | SC10-60 |
| C37 | E | MC | 36 | 28 | SC20-60 |
| C38 | P | FC | 14 | 6 | SC10-75 |
| C39 | SB | M | 12.5 | 5 | SC20-98 |
| C40 | P | FC | 9.5 | 2 | SC10-60 |
| C41 | E | MC | 28 | 20 | SC20-60 |
| C42 | E | MC | 29.5 | 22 | P |
| C43 | E | MC | 21 | 14 | SC10-98 |
| C44 | E | FC | 22.5 | 13 | SC10-75 |
| C45 | P | FC | 24 | 15 | SC20-98 |
| C46 | P, E | F | 28.5 | 16 | P |
| C47 | S | FC | 26.5 | 19 | SC20-60 |
| C48 | E | MC | 39 | 30 | SC10-60 |
| C49 | E | MC | 44.5 | 35 | SC10-98 |
| C50 | S | MC | 42.5 | 36 | SC20-75 |
| C51 | P | FC | 68 | 60 | SC20-98 |
| C52 | S, P | MC | 86 | 78 | P |
| C53 | E | MC | 26 | 17 | SC10-75 |
| C54 | E | M | 44 | 36 | SC10-98 |
| C55 | E | FC | 43.5 | 34 | SC20-98 |
| C56 | P | F | 28.5 | 20 | SC20-75 |
| C57 | S | MC | 29.5 | 21 | SC10-60 |
| C58 | E | FC | 41.5 | 32 | SC20-60 |
| C59 | E | FC | 42.5 | 31 | SC10-98 |
| C60 | S, E | FC | 44 | 36 | P |
| C61 | P | FC | 46.5 | 39 | SC20-60 |
| C62 | S | MC | 57.5 | 48 | SC10-60 |
| C63 | P, E | MC | 58 | 52 | SC10-75 |
| C64 | E | M | 62.5 | 51 | SC20-98 |
| C65 | E | MC | 96 | 56 | SC10-98 |
| C66 | S | FC | 56 | 47 | SC20-75 |
| C67 | P | MC | 9 | 3 | P |
| C68 | SB | MC | 10.5 | 3 | SC20-60 |
| C69 | P | MC | 13 | 5 | SC20-75 |
| C70 | E | MC | 12.5 | 4 | SC10-75 |

P stands for placebo in the above Table.
SB stands for the Birmin cat (sacred cat of Burma.)

EXAMPLE 4

Testing the Analogue Semiochemical

This study utilized two types of material. A commercial scratching post composed of a board having the dimension 25×60 cm covered with a hemp string arranged in the direction of the width to the entire length. The scratching post was covered on part of the surface by yellow peeling paper in the direction of the length that permits the validation that the scratching post was utilized. The paper was changed each 7 to 8 hours that permitted to have 3 measures taken by day. When the paper was replaced it was placed in a different area on the scratching post that was not used during the 8 hours precedent to obtain an alternative dimension. Lacerated or not the papers were replaced and conserved for testing.

A brown glass bottle containing 50 ml of solution of the analogue of the semiochemical in an alcoholic solution without an adjuvant or a placebo was prepared. This product was applied to the scratching post with the aid of a sterile complex and applied using latex gloves. The product was applied using four longitudinal bands occupying the entire length of the scratching post. This application was renewed every day and once a day during the study.

The cats selected for this study were those that already had a habit of using a scratching post. Their scratching post habitual was removed and replaced with the scratching post described above. The study was performed over a period of seven days.

The following parameters were studied:
NPL: the numbers of papers that were lacerated in 7 days
DBFL: the delay before the first laceration
SOA: the number of scratches on another object The NPL permitted to evaluate visually the frequency of new scratches, The DBFL permitted to estimate the number of lacerations with the new scratching post. The SOA permitted to identify the failure leading to the lacerations and then dispensed to other objects besides the scratching post.

The method of evaluation of this study was the following. The evaluation of NPL was done using an evaluation of 1 for all of the papers that had lacerations thereon. A paper that simply became unhooked from the support was given a score of 0, lacking an intact non-lacerated paper. The DBFL was not evaluated until the replacement paper was added. It was taken into account the number of first order paper that was scratched. If no paper was scratched a note of 22 was given. The value of DBFL was between 1 and 22. SOA was evaluated for every scratch that was noted. If no scratches were present then a note of zero was assigned. SOA was thus the sum of the scores during the seven days. A scratch was scored if it was directly observed or if traces of a scratch could be found.

The results are set forth in Table VI below.

TABLE VI

| CATS | TREATMENT | NPL | DBFL | SOA |
| --- | --- | --- | --- | --- |
| C1 | SC10-60 | 3 | 6 | 2 |
| C2 | SC20-98 | 18 | 1 | 0 |
| C3 | SC10-60 | 7 | 3 | 1 |
| C4 | SC10-75 | 9 | 5 | 0 |
| C5 | P | 1 | 5 | 5 |
| C6 | SC20-75 | 20 | 1 | 0 |
| C7 | SC20-98 | 19 | 2 | 0 |
| C8 | P | 0 | 22 | 6 |
| C9 | SC20-60 | 7 | 6 | 2 |
| C10 | SC10-98 | 12 | 3 | 3 |
| C11 | SC10-75 | 4 | 4 | 5 |
| C12 | SC20-75 | 17 | 1 | 0 |
| C13 | SC20-75 | 18 | 1 | 1 |
| C14 | SC10-60 | 3 | 8 | 6 |
| C15 | SC20-60 | 9 | 4 | 2 |
| C16 | SC20-98 | 20 | 1 | 0 |
| C17 | P | 4 | 17 | 4 |
| C18 | SC10-60 | 2 | 7 | 6 |
| C19 | P | 0 | 22 | 7 |
| C20 | SC10-98 | 11 | 6 | 2 |
| C21 | SC10-75 | 3 | 7 | 5 |
| C22 | SC20-98 | 21 | 1 | 0 |
| C23 | SC10-60 | 4 | 9 | 4 |
| C24 | SC10-98 | 6 | 5 | 1 |
| C25 | SC20-60 | 8 | 7 | 3 |
| C26 | SC20-75 | 18 | 2 | 0 |
| C27 | SC10-98 | 6 | 9 | 7 |
| C28 | SC20-98 | 20 | 1 | 0 |
| C29 | SC20-75 | 19 | 1 | 0 |
| C30 | SC10-75 | 6 | 11 | 3 |
| C31 | SC10-60 | 3 | 9 | 6 |
| C32 | SC10-75 | 7 | 8 | 4 |
| C33 | P | 5 | 14 | 7 |
| C34 | SC10-98 | 14 | 3 | 0 |
| C35 | SC20-75 | 19 | 1 | 0 |
| C36 | SC10-60 | 2 | 14 | 6 |
| C37 | SC20-60 | 7 | 6 | 2 |
| C38 | SC10-75 | 6 | 12 | 5 |
| C39 | SC20-98 | 20 | 2 | 0 |
| C40 | SC10-60 | 2 | 18 | 7 |
| C41 | SC20-60 | 6 | 9 | 0 |
| C42 | P | 1 | 15 | 3 |
| C43 | SC10-98 | 17 | 3 | 1 |
| C44 | SC10-75 | 3 | 11 | 3 |
| C45 | SC20-98 | 17 | 3 | 0 |
| C46 | P | 3 | 17 | 7 |
| C47 | SC20-60 | 11 | 8 | 6 |
| C48 | SC10-60 | 5 | 14 | 6 |
| C49 | SC10-98 | 18 | 2 | 1 |
| C50 | SC20-75 | 21 | 1 | 0 |
| C51 | SC20-98 | 20 | 1 | 0 |
| C52 | P | 4 | 16 | 4 |
| C53 | SC10-75 | 9 | 8 | 3 |
| C54 | SC10-98 | 14 | 6 | 3 |
| C55 | SC20-98 | 21 | 1 | 0 |
| C56 | SC20-75 | 17 | 2 | 0 |
| C57 | SC10-60 | 3 | 16 | 7 |
| C58 | SC20-60 | 12 | 6 | 2 |
| C59 | SC10-98 | 15 | 3 | 1 |
| C60 | P | 0 | 22 | 6 |
| C61 | SC20-60 | 9 | 11 | 0 |
| C62 | SC10-60 | 2 | 14 | 1 |
| C63 | SC10-75 | 6 | 9 | 5 |
| C64 | SC20-98 | 18 | 2 | 0 |
| C65 | SC10-98 | 11 | 7 | 5 |
| C66 | SC20-75 | 19 | 1 | 1 |
| C67 | P | 2 | 17 | 7 |
| C68 | SC20-60 | 4 | 14 | 3 |
| C69 | SC20-75 | 15 | 3 | 0 |
| C70 | SC10-75 | 3 | 13 | 7 |

P is the placebo.

Figure 1:
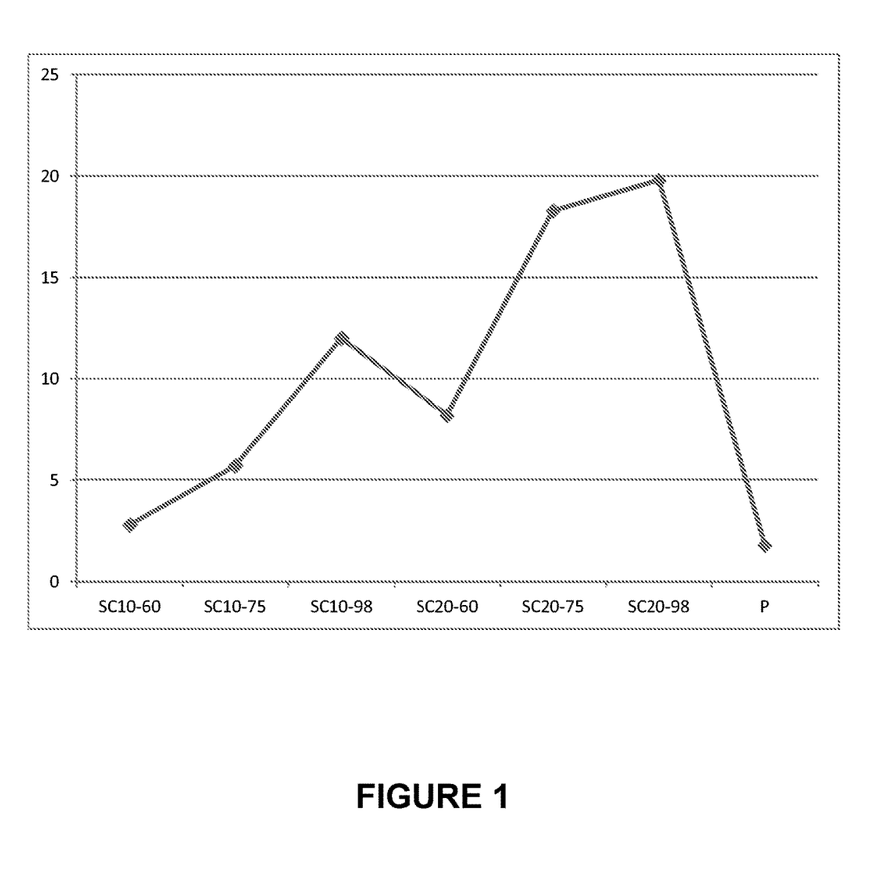
FIG. 1 is a X bar graph with joined points showing the average of the NPL results using the cat scratching semiochemical analogues. The limits of control are 3 Sigma.
Figure 2:
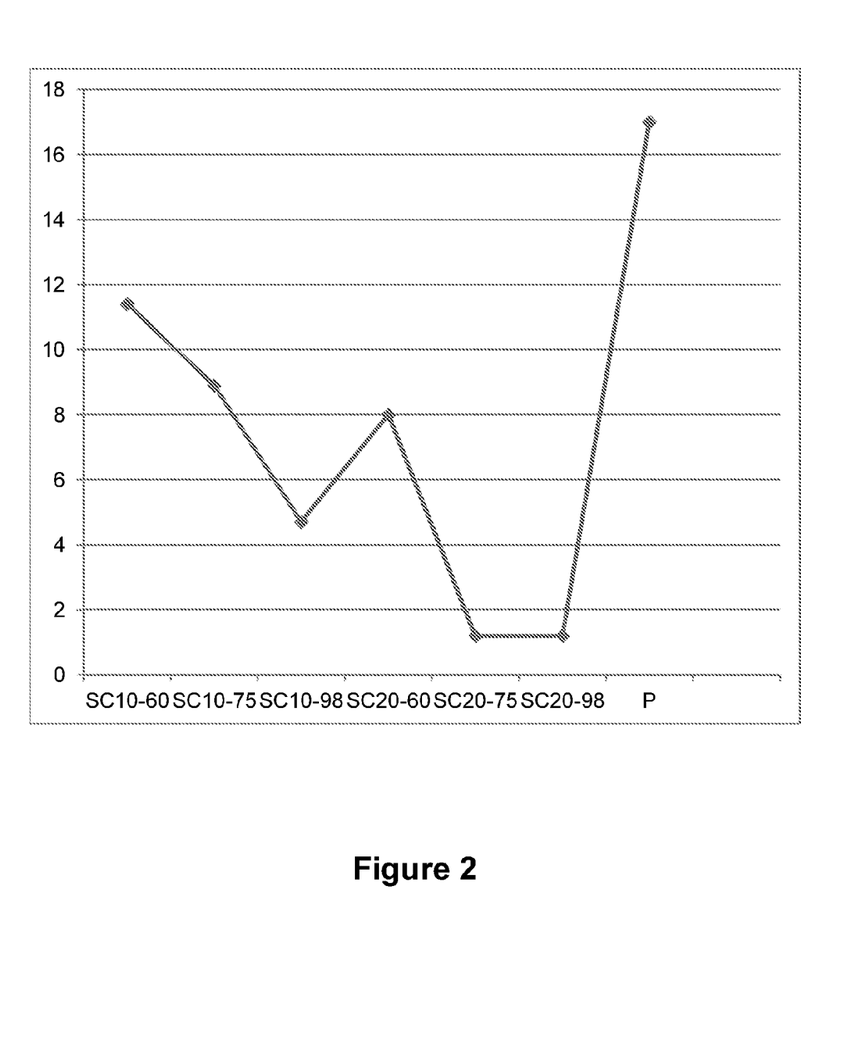
FIG. 2 is a X bar graph with joined points showing the average of the DBFL results using the cat scratching semiochemical analogues. The limits of control are 3 Sigma.
Figure 3:
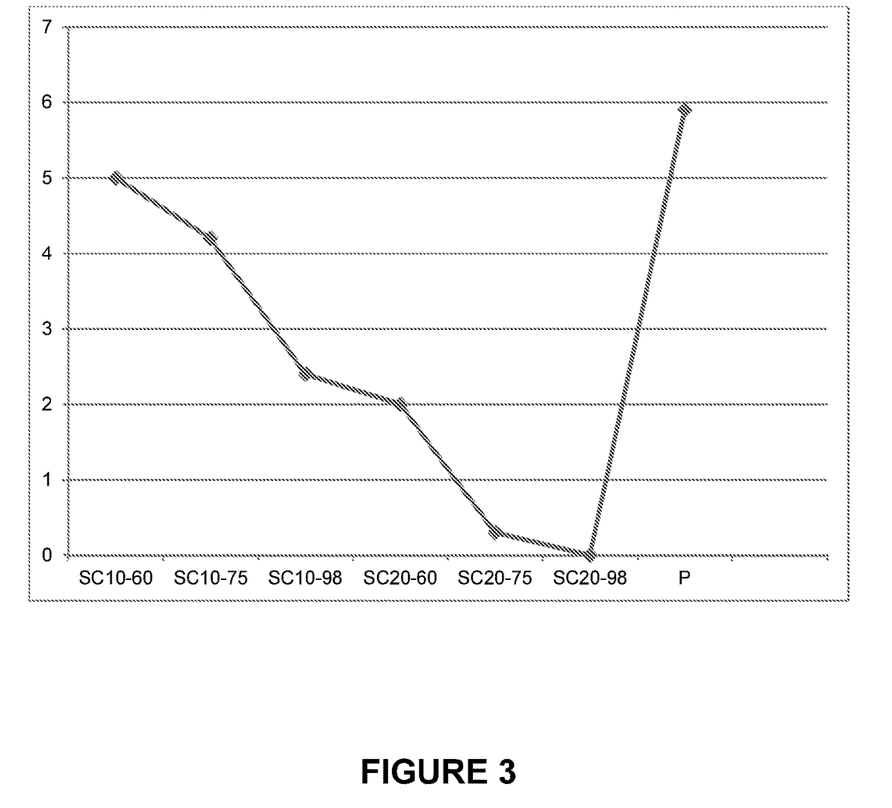
FIG. 3 is a X bar graph with joined points showing the average of the SOA results using the cat scratching semiochemical analogues. The limits of control are 3 Sigma.

The results are set forth in FIGS. 1 to 3. The results of this analysis permit to conclude that solutions SC20-98 and SC20-75 are the semiochemical that were more efficient.

The results of the t tests for SC20-75 and SC20-98 are set forth below.

Unpaired t-Test for NPL Variable Group: Treatment Theoretical Gap=0 for SC20-75, SC20-98

| average gap | DDL | t | p |
|---|---|---|---|
| −1.100 | 18 | −1.601 | 0.1268 |

Information of the Group for NPL Variable Group: Treatment

| treatment | number | average | variance | standard deviation | standard error |
|---|---|---|---|---|---|
| SC20-75 | 10 | 18.300 | 2.900 | 1.703 | 0.539 |
| SC20-98 | 10 | 19.400 | 1.822 | 1.350 | 0.427 |

Unpaired t-Test for DBFL Variable Group: Treatment Theoretical Gap=0 for SC20-75, SC20-98

| average gap | DDL | t | p |
|---|---|---|---|
| −1.00 | 18 | −0.318 | 0.741 |

Information of the Group for DBFL Variable Group: Treatment

| treatment | number | average | variance | standard deviation | standard error |
|---|---|---|---|---|---|
| SC20-75 | 10 | 1.400 | 0.489 | 0.699 | 0.221 |
| SC20-98 | 10 | 1.500 | 0.500 | 0.707 | 0.224 |

Unpaired t-test for SOA variable group: treatment Theoretical gap=0 for SC20-75, SC20-98

| average gap | DDL | t | p |
|---|---|---|---|
| 0.200 | 18 | 1.500 | 0.1510 |

Information of the group for SOA variable group: treatment

| treatment | number | average | variance | standard deviation | standard error |
|---|---|---|---|---|---|
| SC20-75 | 10 | 0.200 | 0.178 | 0.422 | 0.133 |
| SC20-98 | 10 | 0.000 | 0.000 | 0.000 | 0.000 |

This analysis highlighted the absence of any statistically significant difference between the two treatments for all of the parameters that were studied. This confirms the efficacy of the analogs of the scratching pheromone and permitting to discriminate between the different solutions and to choose the solution which is more efficient.

EXAMPLE 5

Optimization of SC20-75

SC20-75 was chosen for this study since it was easier to fabricate at a lower cost than SC20-98. This study was performed to optimize SC20-75 either by using an olfactory adjuvant or by the association with visual signals that reproduce an attractive effect to the cats associated with vertical lacerations and are perfectly mimicked by the presence of vertical stripes such as wallpaper, fabrics etc.

This study was performed on cats that had consultations with two veterinarians at the same clinic and thus was a monocentric study. The cats were described as destructors since they had a behavior of marking by scratching and destroying objects.

To be included in this study, the cats (1) had a behavior of marking by scratching for at least 2 months; (2) were in good health and behavior other than the scratching; (3) were between the ages of 9 months and 8 years; and (4) sex and race were indifferent.

The cats that were not included in this study were those that (1) had onychectomies (declawed) (2) were subjected to a therapy to remove the claws (3) presented somatic or behavior disorders (4) had treatments for psychotropic medications or hormones for at least 6 months (5) cats whose scratching was lessened by semiochemical therapy.

In the course of the study the cats would be excluded for the following reasons: (1) exacerbation of scratching; (2) default of compliance with the study such as paper with the scratch marks not returned; (3) appearance of urinary marking or aggression; (4) were given anesthesia; (5) had a surgical intervention; (6) caught an organic disease; and (7) administration of a drug other than an antiparasite internally or externally.

Sixteen cats were selected for this study that lasted 15 days. E stands for Eurasian, S for Siamese and P for Persian in the table below. The cats had the following characteristics:

TABLE VII

| CATS | RACE | SEX | AGE IN MONTHS | DURATION OF SCRATCHING IN MONTHS |
|---|---|---|---|---|
| C1 | E | MC | 15 | 3 |
| C2 | E | MC | 18 | 3 |
| C3 | E | MC | 26 | 2 |
| C4 | S | FC | 24 | 6 |
| C5 | E | MC | 28 | 4 |
| C6 | P | FC | 27 | 2 |
| C7 | S, E | F | 32 | 6 |
| C8 | P | FC | 11 | 3 |
| C9 | P, E | MC | 9 | 2 |
| C10 | E | FC | 15 | 8 |
| C11 | E | FC | 17 | 5 |
| C12 | E | M | 9 | 2 |
| C13 | P | FC | 10 | 4 |
| C14 | E | MC | 26 | 18 |
| C15 | SB | M | 23 | 14 |
| C16 | E | MC | 9 | 3 |

SB stands for the Birmin cat (sacred cat of Burma.)

The statistics on the group of cats chosen for this study that had the appropriate duration of scratching are as follows:

| | |
|---|---|
| Average | 5.312 |
| Standard Deviation | 4.571 |
| Standard Error | 1.143 |
| Number | 16 |
| Minimum | 2.000 |
| Maximum | 18.000 |
| Number missing | 0 |

The scratching posts were the same as used in Example 4, but two scratching posts were contributed to each cat to respect the methods used in each test. One of the scratching posts was labeled S hidden from the face of the cat. It was coated with the adjuvanted analogue scratching semiochemical from a flask also marked S. The other scratching post was marked A and was coated with an adjuvanted alcohol from a flask marked A.

The 50 ml solutions of analogue scratching semiochemical were contained in a brown glass flask and contained SC20-75 adjuvanted with a 10% of tincture of catnip. The control was a solution of 95% alcohol adjuvanted with tincture of catnip at 10% of the total volume. The scratching posts were coated as in Example 4. The paper that was utilized on the scratching post was the same as in Example 4.

To compare the efficacy of the two scratching posts, they were placed 60 centimeters apart and on either side of a surface that was previously scratched. The scratching post (S) had the semiochemical analogue coated thereon, while the post (A) was coated with the control. Like in Example 4 a part of the scratching post was recovered with peeling paper to detect the scratches. In this case the papers were also placed according to the same modalities on the object that was already scratched by the cat. One sole object (if there were many) was left accessible to the cat, which is the object that should be the most scratched. The evaluation was based on this object. The study was performed for a period of 7 days.

The evaluation of this study was done with the same parameters as that set forth in Example 4 with the exception of SOA that was replaced by the measure of the object that was habitually scratched by the cat (OL). This object was considered as the place of scratching in competition with the other scratching posts of the cat.

The results are set forth in Table VIII below for the study done with the analogue of cat scratch semiochemical (S).

TABLE VIII

| CATS | NPL | DBFL |
|------|-----|------|
| C1   | 17  | 1    |
| C2   | 18  | 2    |
| C3   | 15  | 1    |
| C4   | 19  | 2    |
| C5   | 20  | 1    |
| C6   | 18  | 3    |
| C7   | 19  | 1    |
| C8   | 21  | 1    |
| C9   | 18  | 2    |
| C10  | 15  | 4    |
| C11  | 18  | 2    |
| C12  | 19  | 1    |
| C13  | 19  | 1    |
| C14  | 19  | 1    |
| C15  | 20  | 1    |
| C16  | 17  | 3    |

The results are set forth below in Table IX for the control (A).

TABLE IX

| CATS | NPL | DBFL |
|------|-----|------|
| C1   | 2   | 9    |
| C2   | 2   | 15   |
| C3   | 1   | 18   |
| C4   | 0   | 22   |
| C5   | 3   | 7    |
| C6   | 1   | 17   |
| C7   | 1   | 18   |
| C8   | 2   | 14   |
| C9   | 1   | 12   |
| C10  | 3   | 16   |
| C11  | 1   | 17   |
| C12  | 3   | 14   |
| C13  | 0   | 22   |
| C14  | 0   | 22   |
| C15  | 1   | 16   |
| C16  | 0   | 22   |

The results are set forth below in Table X for the object that was habitually scratched by the cat (OL).

TABLE X

| CATS | NPL | DBFL |
|------|-----|------|
| C1   | 14  | 1    |
| C2   | 11  | 1    |
| C3   | 15  | 1    |
| C4   | 9   | 3    |
| C5   | 10  | 2    |
| C6   | 6   | 1    |
| C7   | 13  | 1    |
| C8   | 8   | 1    |
| C9   | 14  | 2    |
| C10  | 15  | 1    |
| C11  | 3   | 2    |
| C12  | 6   | 2    |
| C13  | 4   | 1    |
| C14  | 8   | 1    |
| C15  | 8   | 1    |
| C16  | 3   | 2    |

Figure 4:
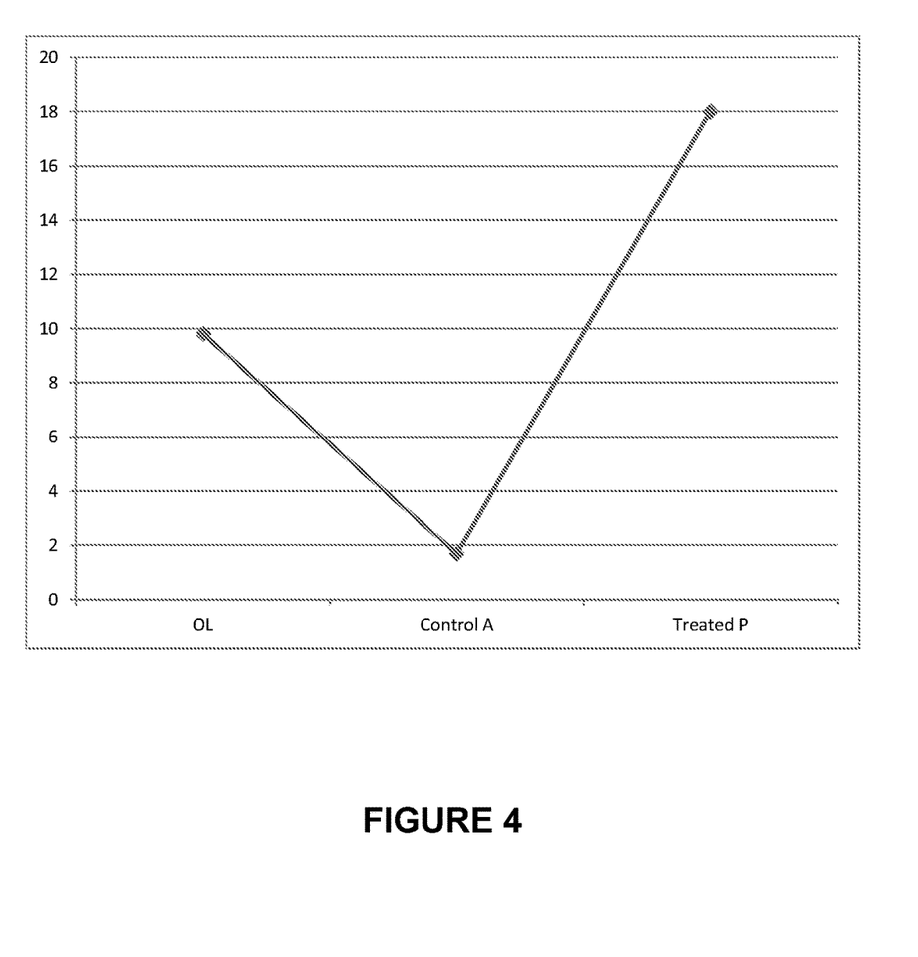
FIG. 4 is a X bar graph with joined points showing the average of the NPL results using the cat scratching semiochemical analogues. The limits of control are 3 Sigma. OL stands for the object that the cat habitually lacerated. The mean value is 9.583, the inferior value from the mean value is 7.576, while the superior value from the mean value is 11.591.
Figure 5:
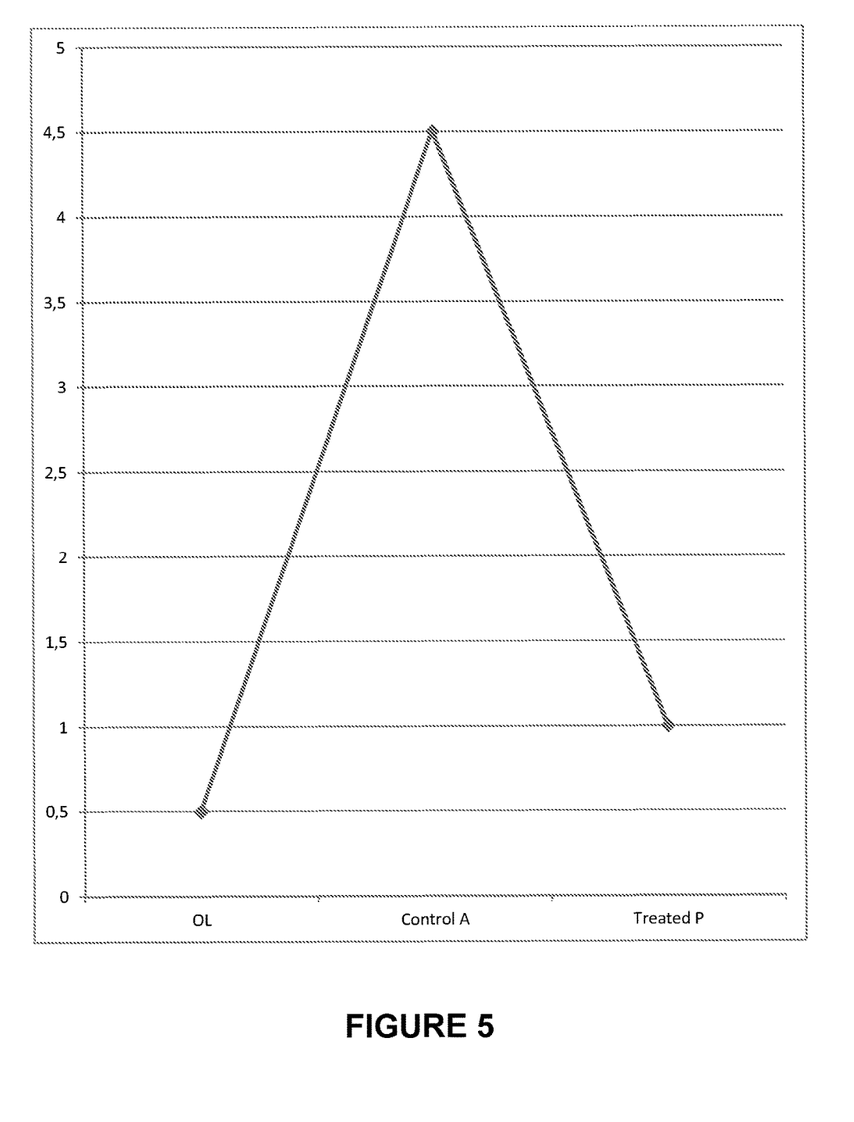
FIG. 5 is a X bar graph with joined points showing the average of the DBFL results using the cat scratching semiochemical analogues. The limits of control are 3 Sigma. OL stands for the object that the cat habitually lacerated. The mean value is 2.665, the inferior value from the mean value is 1.194, while the superior value from the mean value is 4.137.

The results are shown in FIGS. 4 and 5.

Statistical analysis was then performed using the above results.

Analogue Scratch Semiochemical SC20-75

| Test | Average | Standard Deviation | Standard Error | Number | Minimum | Maximum | Number missing |
|------|---------|--------------------|----------------|--------|---------|---------|----------------|
| NPL  | 18.250  | 1.653              | 0.4313         | 16     | 15.000  | 21.000  | 0              |
| DBFL | 1.688   | 0.946              | 0.237          | 16     | 1.000   | 4.000   | 0              |

Control (A)

| Test | Average | Standard Deviation | Standard Error | Number | Minimum | Maximum | Number missing |
|------|---------|--------------------|----------------|--------|---------|---------|----------------|
| NPL  | 1.312   | 1.078              | 0.270          | 16     | 000     | 3.000   | 0              |
| DBFL | 16.312  | 4.527              | 1.132          | 16     | 7.000   | 22.000  | 0              |

The Object that was Habitually Scratched by the Cat

| Test | Average | Standard Deviation | Standard Error | Number | Minimum | Maximum | Number missing |
|------|---------|--------------------|----------------|--------|---------|---------|----------------|
| NPL  | 9.188   | 4.167              | 1.042          | 16     | 3.000   | 15.000  | 0              |
| DBFL | 1.438   | 0.629              | 0.157          | 16     | 1.000   | 3.000   | 0              |

The SC20-75 analogue of feline interdigital semiochemicals was tested in sixteen (16) cats. Those cats were described as scratching intensively at home by their owners. For each cat, the owners were asked to define a "target area" which was a place where the cat had intensive scratching activity. Two cardboard scratching posts were fixed 60 cm on each side of the target area. One of those scratching posts was coated with a placebo and the other the semiochemical solution. The assessment parameter was the total number of scratches during 7 days of the study, counted by putting a piece of paper on half of the scratching surfaces. Comparison was made using the Mann-Whitney test.

The scratching post sprayed with the semiochemical was used more by the cats in a significant way when compared to the target area ($p<0.05$) and in a very highly significant way when compared to the target area ($p<0.001$).

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents.

The invention claimed is:

1. A method for preventing a cat from scratching on one or more objects that the cat uses for scratching, said method comprising applying to the one or more objects a suitable amount of a semiochemical composition comprising effective amounts of valeric acid, lactic acid, and linoleic acid.

2. The method according to claim 1, wherein the semiochemical composition comprises between about 3.5% to 10.5% (w %/w %) of valeric acid, between about 5.5% to 15.5% (w %/w %) of lactic acid and between 68.5% to 83.5 (w %/w %) of linoleic acid.

3. The method according to claim 1, wherein the semiochemical composition further comprises oleic acid.

4. The method according to claim 3, wherein the semiochemical composition comprises between about 3.5% to 10.5% (w %/w %) of valeric acid, between about 5.5% to 15.5% (w %/w %) of lactic acid, between 68.5% to 83.5 (w %/w %) of linoleic acid, and about 20.1% to 24.5% (w %/w %) of oleic acid.

5. The method according to claim 1, wherein the semiochemical composition further comprises a cat attractant.

6. The method according to claim 5, wherein the cat attractant is catnip.

7. The method according to claim 1, wherein the semiochemical composition is in the form of a solution and further comprises a solvent.

8. The method according to claim 7, wherein the solvent is a nonaqueous solvent.

9. The method according to claim 8, wherein the nonaqueous solvent is selected from the group consisting of an alcohol and propylene glycol.

10. The method according to claim 9, wherein the nonaqueous solvent is propylene glycol.

* * * * *